United States Patent
Sugiyama et al.

(10) Patent No.: US 11,964,043 B2
(45) Date of Patent: Apr. 23, 2024

(54) METHOD OF EMULSIFICATION USING CORE-CORONA TYPE MICROPARTICLES

(71) Applicant: SHISEIDO COMPANY, LTD., Tokyo (JP)

(72) Inventors: Yuki Sugiyama, Yokohama (JP); Ryushi Fukuhara, Yokohama (JP); Yang Han, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 245 days.

(21) Appl. No.: 17/362,206

(22) Filed: Jun. 29, 2021

(65) Prior Publication Data

US 2021/0330573 A1 Oct. 28, 2021

Related U.S. Application Data

(62) Division of application No. 16/336,398, filed as application No. PCT/JP2017/032926 on Sep. 12, 2017, now abandoned.

(30) Foreign Application Priority Data

Sep. 27, 2016 (JP) ................... 2016-188437

(51) Int. Cl.
*A61K 8/91* (2006.01)
*A61K 8/00* (2006.01)
(Continued)

(52) U.S. Cl.
CPC .................. *A61K 8/91* (2013.01); *A61K 8/00* (2013.01); *A61K 8/06* (2013.01); *A61K 8/068* (2013.01);
(Continued)

(58) Field of Classification Search
CPC combination set(s) only.
See application file for complete search history.

(56) References Cited

U.S. PATENT DOCUMENTS

| | | | | |
|---|---|---|---|---|
| 2008/0286218 A1* | 11/2008 | Giroud | ..................... | A61K 8/91 |
| | | | | 424/70.13 |
| 2012/0076746 A1* | 3/2012 | Tate | ........................ | C08L 33/26 |
| | | | | 424/70.2 |

(Continued)

FOREIGN PATENT DOCUMENTS

CN 104159662 A 11/2014
EP 0372546 A2 * 7/1989
(Continued)

OTHER PUBLICATIONS

Russian Search Report, App. No. 2019111111/04 (021588), dated Dec. 11, 2020, 2 pages—Russia.
(Continued)

*Primary Examiner* — Peter A Salamon
(74) *Attorney, Agent, or Firm* — Andrew F. Young; NOLTE LACKENBACH SIEGEL

(57) ABSTRACT

A method of emulsification of an oil phase in an aqueous continuous phase, by dispersing core-corona microparticles into the aqueous phase, adding the oil phase, and applying shearing force for a time sufficient to emulsify the resulting mixture. The core-corona microparticles are obtained by radical co-polymerization of a polyethylene oxide macromonomer with at least one hydrophobic acrylate monomer and at least one hydrophobic acrylamide monomer.

10 Claims, 2 Drawing Sheets

(51) Int. Cl.
    *A61K 8/06*    (2006.01)
    *A61K 8/81*    (2006.01)
    *A61K 8/86*    (2006.01)
    *A61Q 1/00*    (2006.01)
    *A61Q 5/00*    (2006.01)
    *A61Q 17/04*    (2006.01)
    *A61Q 19/00*    (2006.01)
    *C08F 290/06*    (2006.01)

(52) U.S. Cl.
    CPC .................. *A61K 8/81* (2013.01); *A61K 8/86* (2013.01); *A61Q 1/00* (2013.01); *A61Q 5/00* (2013.01); *A61Q 17/04* (2013.01); *A61Q 19/00* (2013.01); *C08F 290/06* (2013.01); *C08F 290/062* (2013.01)

(56) References Cited

U.S. PATENT DOCUMENTS

| | | | |
|---|---|---|---|
| 2012/0302476 | A1 | 11/2012 | Koschabek et al. |
| 2013/0171084 | A1* | 7/2013 | Kawaratani ............... A61K 8/89 424/63 |
| 2014/0242014 | A1* | 8/2014 | Bukawa ............... A61K 8/8152 424/64 |
| 2014/0343170 | A1* | 11/2014 | Sugiyama ............... A61Q 13/00 512/2 |
| 2014/0364511 | A1 | 12/2014 | Chari et al. |
| 2016/0001244 | A1* | 1/2016 | Sugiyama ............... C08L 33/12 512/1 |

FOREIGN PATENT DOCUMENTS

| | | |
|---|---|---|
| EP | 0372546 | 12/1989 |
| EP | 2796193 | 10/2014 |
| FR | 2957791 | 9/2011 |
| JP | 61-278350 | 12/1986 |
| JP | 2001-518111 | 10/2001 |
| JP | 2002-302696 | 10/2002 |
| JP | 2005-15623 | 1/2005 |
| JP | 2006-161026 | 6/2006 |
| JP | 2010-59076 | 3/2010 |
| JP | 4577721 | 11/2010 |
| JP | 5207424 | 6/2013 |
| JP | 2013-147486 | 8/2013 |
| JP | 2014-534275 | 12/2014 |
| RU | 2012135375 A | 2/2014 |
| TW | 201334794 A1 | 9/2013 |
| WO | WO 03/082999 | 10/2003 |
| WO | WO 2004/096422 | 11/2004 |
| WO | WO 2017/057563 | 4/2017 |

OTHER PUBLICATIONS

Indian Office Action. , App. No. 201917016553, dated Nov. 25, 2020, 7 pages—Indian, 7 pages—English.
Russian Office Action, App. No. 201911111/04(021588) dated Dec. 11, 2020, 15 pages—Russia, 14 pages—English.
Extended European Search Report dated Apr. 1, 2020, 10 pages.
PCT/JP2017/032926, ISR and Writen Opinion dated Dec. 12, 2017, 11 pages—Japanese, 14 pages—English.
B. Binks, et al, Advances in Colloid and Interface Science, 100-102 (2003) Advances in Colloid and Interface Science, vols. 100-102, Feb. 28, 2003, pp. 503-546, Emulsions stabilized soley by colloidal particles, Robert Aveyard, Binks, Clint, www.sciencedirect.com dated Mar. 26, 2019.
J. Colloid Interface Sci., 274, 49 (2004), 49-54 Swelling behavior of PMMA-g-PEO microgel particles by organic solvents, Isamu Kaneda and Brian Vicent, www.sciencedirect.com.
TW 106132434, Taiwan Office Action dated Sep. 17, 2021, 5 pages—English, 6 pages—Chinese.
CN 201780059745.7, Chinese Office Action dated Jun. 2, 2021, 6 pages—Chinese; 7 pages—English.

* cited by examiner

METHOD OF EMULSIFICATION USING CORE-CORONA TYPE MICROPARTICLES

RELATED APPLICATION

This application is a divisional of U.S. patent application Ser. No. 16/336,398, filed Mar. 25, 2019, which relates to and claims the priority of Ser. No. PCT/JP2017/032926, filed Sep. 12, 2017, the entire contents of which are incorporated herein by reference and which in turn claims priority of Japanese Patent Application serial No. 2016-188437, filed on Sep. 27, 2016 the disclosure of which is incorporated herein by reference.

FIELD OF THE INVENTION

The present invention relates to a cosmetic raw material, and more specifically to a cosmetic raw material comprised of core-corona type microparticles and an oil-in-water emulsified cosmetic using the same.

BACKGROUND OF THE INVENTION

Recently, with the increase in the number of consumers who concern for safety, cosmetics that do not substantially comprise surfactants tend to be preferred. Further, since blending a large amount of surfactants causes stickiness, there is a demand for an emulsification method without relying on surfactants.

As a method of preparing an oil-in-water emulsion without surfactants, a Pickering emulsion method that emulsifies by adhering a powder to an interface between an oil phase and an aqueous phase is known (for example, Patent Literature 1 and Non-patent literature (1)). Inorganic powders such as metal oxides, minerals (for example, silica) or the like are widely used as the afore-mentioned powder; however, emulsification capability of these powders is weak and the powder needs to be blended in a large amount. Thus, powdery or squeaky feeling in the resulting cosmetic was problematic. Further, since oil droplets emulsified by inorganic powders are weak against impact and are easily united by stirring or vibration, low emulsification stability of the cosmetic was problematic.

Hence, an emulsification method using a core-corona type microgel was proposed by the present inventors. The core-corona type microgel is a particle formed by crosslinking one or more polymer(s) and has a structure of which the hydrophilic region is exposed to the surface of the core part where the hydrophobic region of the polymer is crosslinked and spheroidized thereto. When the core-corona type microgel absorbs a solvent, it swells and becomes a gel-state. Thus, it has been mainly used as thickeners or coating agents in the field of cosmetics (Non-patent Literature 2).

The present inventors found that the core-corona type microgel obtained by radically polymerizing a specific polyethylene oxide macromonomer, a specific acrylate derivative monomer, and a specific crosslinking monomer under a certain condition has a high swelling property to an organic solvent and can stably emulsify various types of oil components. Further, they reported that by using the afore-mentioned microgel as an emulsifier, an oil-in-water emulsified cosmetic that is excellent in emulsification stability, less in stickiness, and less in powdery or squealy feeling can be obtained (Patent Literatures 2 to 4).

However, when the crosslink density of the core part of the afore-mentioned microgel is low, the core-structure collapses during swelling, and when the crosslink density is too high, the microgel aggregates. In either case, there was a problem that the afore-mentioned microgel did not function as an emulsifier.

CITATION LIST

Patent Literatures

Patent Literature 1: Japanese Unexamined Patent Publication No. 2001-518111A
Patent Literature 2: Japanese Unexamined Patent Publication (Translation of PCT Application) No. 2006-161026A
Patent Literature 3: Japanese Patent No. 4577721B
Patent Literature 4: Japanese Patent No. 5207424B

Non-Patent Literatures

Non-Patent Literature 1: B. Binks et. al, Advances in Colloid and Interface Science, 100-102 (2003).
Non-Patent Literature 2: J. Colloid Interface Sci., 274, 49 (2004).

DISCLOSURE OF THE INVENTION

Technical Problem

The present invention has been made in view of the conventional art, and an object thereof is to provide an emulsifier comprised of core-corona type microparticles that emulsification capability thereof is not affected by the crosslinking level and an oil-in-water emulsified cosmetic emulsified by the afore-mentioned emulsifier.

Solution to the Problem

The present inventors have diligently investigated on the afore-mentioned problem, and as a result, they have found that a core-corona type microparticle that can be widely used as an oil-in-water emulsifier can be obtained by radically polymerizing a specific acrylamide derivative and a specific acrylate derivative without crosslinking under certain conditions. Further, they have also found that an oil-in-water emulsified cosmetic emulsified by the afore-mentioned microparticles is excellent in emulsification stability, less in stickiness, less in powdery or squeaky feeling, and also excellent in water-washability, and completed the present invention.

That is, the present invention comprises the following.

[1] It is comprised of core-corona type microparticles that is obtained by radical polymerization of a polyethylene oxide macromonomer represented by a chemical formula (1), and at least one hydrophobic monomer selected from a group of an acrylate derivative monomer represented by a chemical formula (2) and an acrylamide derivative monomer represented by a chemical formula (3) under the following conditions (A) to (D);

(A) a molar ratio expressed by a feed molar amount of the polyethylene oxide macromonomer/a feed molar amount of (the acrylate derivative monomer and/or the acrylamide derivative monomer) is 1:10 to 1:250;

(B) the macromonomer represented by the chemical formula (1) is at least one derivative selected from a group consisting of an acrylic acid derivative and a methacrylic acid derivative that have a polyethylene glycol group with 8 to 200 repeating units, the acrylate derivative monomer represented by the following formula (2) is at least one monomer selected from a group consisting of an acrylic acid derivative and a methacrylic acid derivative that have a substituent comprising an alkyl group having 1 to 12 carbon atoms, and the acrylamide derivative monomer represented by the chemical formula (3) is at least one monomer selected from a group consisting of an acrylamide derivative and a methacrylamide derivative that have a substituent comprising an alkyl group having 1 to 18 carbon atoms;
(C) a polymerization solvent is a mixture of alcohol and water, wherein the alcohol is at least one alcohol selected from a group consisting of ethanol, dipropylene glycol, 1,3-butylene glycol and isoprene glycol; and
(D) a solvent composition of the water-alcohol mixed solvent is water:alcohol=90 to 10:10 to 90 in a mass ratio at 20° C.;

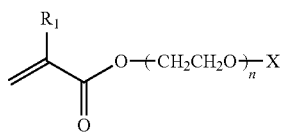

(1)

wherein $R_1$ is at least one substitute selected from a group consisting of H and an alkyl group having 1 to 3 carbon atoms, n is a number of 8 to 200, and X is at least one substitute selected from a group consisting of H and $CH_3$;

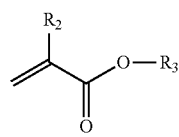

(2)

wherein $R_2$ is at least one substitute selected from a group consisting of H and an alkyl group having 1 to 3 carbon atoms, and $R_3$ is a substituent that has an alkyl group having 1 to 12 carbon atoms;

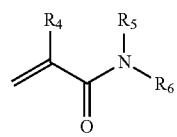

(3)

wherein $R_4$ is at least one substitute selected from a group consisting of H and an alkyl group having 1 to 3 carbon atoms, and both $R_5$ and $R_6$ are one substitute selected from a group consisting of H and substituents that have an alkyl group having 1 to 18 carbon atoms.
[2] A cosmetic raw material according to [1], wherein a particle size of the core-corona type microparticle is in a rage of 50 to 400 nm.
[3] An emulsifier comprised of the cosmetic raw material according to [1] or [2].

[4] An oil-in-water emulsified cosmetic emulsified by the emulsifier according to [3].
[5] A clouding agent comprised of the cosmetic raw material according to [1] or [2].

Effect of the Invention

The present invention provides an emulsifier comprised of uncrosslinked core-corona type microparticles. Further, by using the afore-mentioned emulsifier, an oil-in-water emulsified cosmetic that is excellent in emulsification stability, less in stickiness, less in powdery or squeaky feeling, and excellent in water-washability is provided.

MODE FOR CARRYING OUT THE INVENTION

Figure 1:
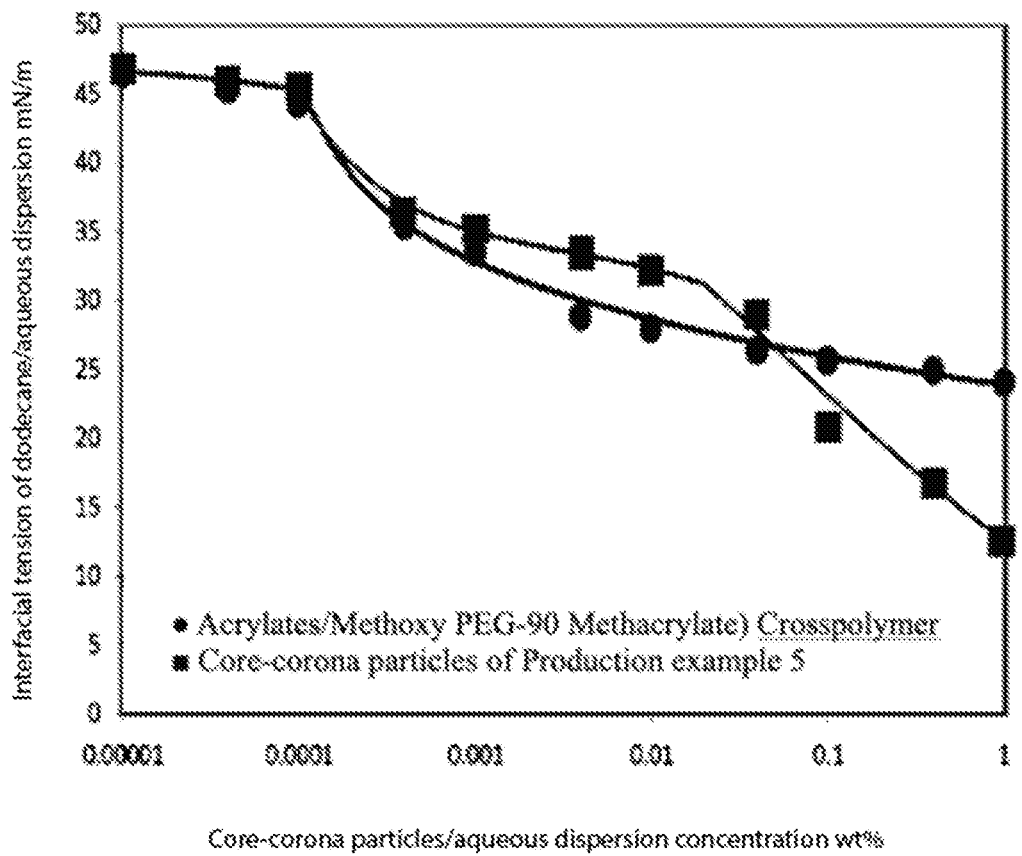
FIG. 1 is a graph that depicts an analysis of an effect on oil/aqueous interfacial tension with respect to the core-corona type microparticles (Production Example 5) according to the present invention and the conventional crosslinked core-corona type microparticles ((Acrylates/Methoxy PEG-90 Methacrylate) Crosspolymer).
Figure 2:
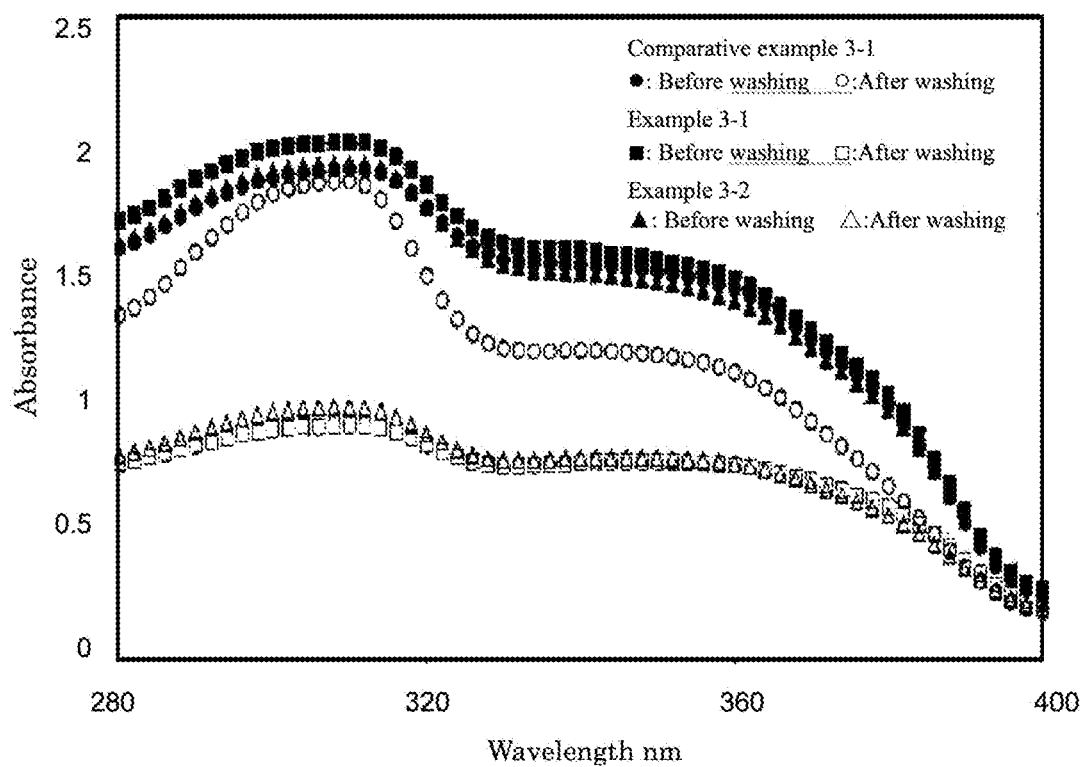
FIG. 2 is a graph that depicts an analysis for water-washability with respect to the cosmetics of the Examples and the comparative examples.

In the following, (I) the cosmetic raw material of the present invention and (II) the use of the afore-mentioned raw material will be described.
(I) Cosmetic Raw Material
The cosmetic raw material according to the present invention is a dispersion of core-corona type microparticles obtained by radically polymerizing monomers represented by the following formulae (1) to (3) under specific conditions.

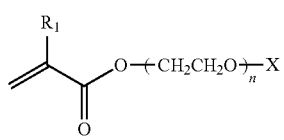

(1)

$R_1$ is an alkyl group having 1 to 3 carbon atoms, and n (the molecular weight of the polyethylene oxide part) is a number of 8 to 200. X is H or $CH_3$.
The polyethylene oxide macromonomers of chemical formula (1) is preferably an acrylic acid derivative or a methacrylic acid derivative. For the polyethylene oxide macromonomers, commercial products commercially available from Aldrich or BLEMMER® sold by NOF Corporation can be used. Such examples of macromonomers include PME-400, PME-1000, and PME-4000 (n values in chemical formula (1) are 9, 23 and 90, respectively, all products from NOF Corporation), which are methoxy polyethylene glycol monometalate.

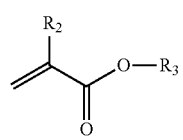

(2)

$R_2$ is an alkyl group having 1 to 3 carbon atoms, and $R_3$ is a substituent including an alkyl group having 1 to 12 carbon atoms.

The hydrophobic monomers of chemical formula (2) is preferably an acrylic acid derivative or a methacrylic acid derivative, and methyl acrylate, ethyl acrylate, propyl acrylate, butyl acrylate, pentyl acrylate, hexyl acrylate, heptyl acrylate, octyl acrylate, decyl acrylate, dodecyl acrylate, methyl methacrylate, ethyl methacrylate, propyl methacrylate, butyl methacrylate, pentyl methacrylate, hexyl methacrylate, heptyl methacrylate, octyl methacrylate, decyl methacrylate, dodecyl methacrylate and the like may be used, for example. Among these compounds, methyl methacrylate, butyl methacrylate, and octyl methacrylate are particularly preferable.

These hydrophobic monomers are commodity raw materials and they can also be obtained easily as general industrial raw materials. Commercial products commercially available from Aldrich or Tokyo Chemical Industry Co., Ltd may be used, for example.

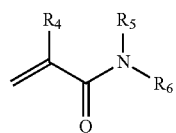

(3)

$R_4$ is H or an alkyl group having 1 to 3 carbon atoms, and $R_5$ and $R_6$ are H or a substituent including an alkyl group having 1 to 18 carbon atoms.

A hydrophobic monomer represented by the formula (3) is preferably an acrylamide derivative or a methacrylamide derivative. For example, t-butylacrylamide, N,N-dimethylacrylamide, N-[3-(dimethylamino)propyl]acrylamide, t-butylmethacrylamide, octylacrylamide, octylmethacrylamide, octadecylacrylamide or the like can be used preferably. Among these, t-butylacrylamide, N,N-dimethylacrylamide and N-[3-(dimethylamino)propyl]acrylamide are particularly preferable.

These hydrophobic monomers are available as commercial products or industrial raw materials.

The copolymer that constitutes the core-corona type microparticles according to the present invention is a copolymer obtained by copolymerizing a macromonomer represented by the formula (1) and one or two or more selected from hydrophobic monomers represented by the formulae (2) and (3) by any radical polymerization method in accordance with the following conditions of (A) to (D).

(A) a molar ratio expressed by a feed molar amount of the polyethylene oxide macromonomer/a feed molar amount of (the acrylate derivative monomer and/or the acrylamide derivative monomer) is 1:10 to 1:250;

(B) the macromonomer represented by the following formula (1) is an acrylic acid derivative or a methacrylic acid derivative having a polyethylene glycol group with 8 to 200 repeating units, the acrylate derivative monomer represented by the following formula (2) is an acrylic acid derivative or a methacrylic acid derivative having a substituent comprising an alkyl group having 1 to 12 carbon atoms, and the acrylamide derivative monomer represented by the following formula (3) is an acrylamide derivative or a methacrylamide derivative having a substituent comprising an alkyl group having 1 to 18 carbon atoms;

(C) a polymerization solvent is a water-alcohol mixed solvent, and the alcohol is one or two or more selected from ethanol, dipropylene glycol, 1,3-butylene glycol and isoprene glycol; and (D) a solvent composition of the water-alcohol mixed solvent is water:alcohol=90 to 10:10 to 90 in a mass ratio at 20° C.

Each condition will be described in detail below.

(Condition (A))

For the feed molar amount of the polyethylene oxide macromonomer and the hydrophobic monomer (i.e., the sum total of the acrylate derivative monomer and/or acrylamide derivative monomer), it can be polymerized when the molar ratio of the feed molar amount of the polyethylene oxide macromonomer/feed molar amount of the hydrophobic monomers is in the range of 1/1 to 10/250 (molar ratio). The feed molar amount is preferably in a range of 1/1 to 10/200 and more preferably in a range of 1/11 to 25/100.

When the molar amount of the hydrophobic monomer is less than 10 times of that of the polyethylene oxide macromonomer, the polymerized polymer becomes water soluble and does not form a core-corona type microgel. In addition, when the molar amount of the hydrophobic monomer is 250 times or more of that of the polyethylene oxide macromonomer, the dispersion stabilization by the polyethylene oxide macromonomer becomes insufficient, so that the hydrophobic polymer due to the insoluble hydrophobic monomer may aggregate and precipitate.

(Condition (B))

A condition (B) has the three conditions (B-1) to (B-3) as shown below.

(B-1)

The macromonomer represented by the formula (1) is an acrylic acid derivative or a methacrylic acid derivative having a polyethylene-glycol group with 8 to 200 repeating units. When the number of the repeating units is 7 or less, particles that are dispersed stably in a solvent may not be obtained. When the number of the repeating units is more than 200, particles become fine and may be unstable when the composition is blended in a cosmetic.

(B-2)

The acrylate derivative monomer represented by the formula (2) is an acrylic acid derivative or a methacrylic acid derivative having a substituent including an alkyl group having 1 to 12 carbon atoms. When the number of carbon atoms is zero (a monomer without a terminal ester bond), the monomer may be too hydrophilic to be emulsion-polymerized adequately. Meanwhile, when the number of carbon atoms is 13 or more, a preferable feeling in use may not be obtained.

(B-3)

The acrylamide derivative monomer represented by the formula (3) is an acrylamide derivative or a methacrylamide derivative having substituents including an alkyl group having 1 to 18 carbon atoms.

The hydrophobic monomers according to the present invention need to have a monomer composition obtained by mixing one or two or more selected from an acrylate derivative monomer represented by the formula (2) and an acrylamide derivative monomer represented by the formula (3).

In the present invention, two types of a methacrylate and a butyl methacrylate or four types of a methacrylate, t-butylacrylamide, N,N-dimethylacrylamide and N-[3-(dimethylamino)propyl]acrylamide are particularly preferably used as hydrophobic monomers. In the combinations of these hydrophobic monomers, it is preferred to additionally use methoxy polyethylene glycol monometalate as a macromonomer.

In the present invention, the most preferable combinations of a macromonomer and hydrophobic monomers include, but are not limited thereto:

methoxy polyethylene glycol monometalate having a polyethylene glycol group with 8 to 90, most preferably 15 repeating units, a methacrylate and a butyl methacrylate;

methoxy polyethylene glycol monometalate having a polyethylene glycol group with 8 to 200, most preferably 90 repeating units, a methyl methacrylate, a butyl methacrylate, t-butylacrylamide and N,N-dimethylacrylamide; and N-[3-(dimethylamino)propyl]acrylamide, t-butylmethacrylamide, octylacrylamide, octylmethacrylamide and octadecylacrylamide.

(Condition (C))

It is necessary that the polymerization solvent is a water-alcohol mixed solvent. The preferable alcohol is the one that can dissolve a hydrophobic monomer represented by chemical formulae (2) and (3). Therefore, one or more selected from ethanol, dipropylene glycol, 1,3-buthylene glycol, and isoprene glycol are preferable.

(Condition (D))

It is preferred that the solvent composition of the water-alcohol mixed solvent, used as the polymerization solvent, is water/alcohol=a range of 90/10 to 10/90, and more preferably a range of 80/20 to 20/80, in the mass ratio at 20° C. When the mix volume of alcohol is lower than 10% by volume, the dissolution of the hydrophobic monomer becomes extremely poor, so that micro particle may not be formed. When the mix volume of alcohol exceeds 90% by volume, an emulsion of the hydrophobic monomer cannot be formed by hydrophobic interaction, so that no emulsion polymerization can proceed and micro particle may not be obtained.

(II) Use

The cosmetic raw material according to the present invention has polyethylene oxide chains, which are nonionic polymers, on its surface and thus is stably dispersed in water. Further, under a condition where both of an oil phase component and an aqueous phase component are present, the core part absorbs the oil phase component and swells and the corona part, which is a core surface, adheres to the interface of the oil phase component and the aqueous phase component because it is compatible with the aqueous component. Therefore, an oil-in-water emulsion system of which oil droplets having the cosmetic raw materials according to the present invention adhered to their surface are dispersed in the aqueous component can be obtained by an ordinary emulsification method (emulsification by stirring and mixing the oil phase component and the aqueous phase component). Since the afore-mentioned oil droplets do not easily unite by further stirring or impact caused by vibration, it is significantly stable compared to the conventional Pickering emulsion that uses inorganic powders.

Accordingly, the cosmetic raw material according to the present invention can preferably be used as an emulsifier for oil-in-water emulsification. The cosmetic raw material according to the present invention does not cause stickiness like ordinary surfactants, and does not cause powdery or squealy feelings like inorganic powders. Furthermore, since it is a Pickering emulsion method, a wide range of types of oil components can be emulsified.

(Oil-in-Water Emulsified Cosmetic)

The oil-in-water emulsified cosmetic according to the present invention is one which is emulsified by the cosmetic raw material comprised of the afore-mentioned core-corona type microparticles. "Emulsified" as used herein can be said as "a state where the microparticles are present in the interface between the oil droplet and the aqueous phase (continuous phase)". The oil-in-water emulsified cosmetic according to the present invention is emulsified by the afore-mentioned microparticles so that it is excellent in emulsification stability, less in stickiness, and less in powdery or squeaky feeling.

The blending amount of the cosmetic raw material of the present invention in a cosmetic is 0.01 to 10% by mass, more preferably 0.05 to 5% by mass, and further more preferably 0.05 to 2% by mass in terms of the pure content of the core-corona type microparticles relative to the total amount of the cosmetic. When the blending quantity is less than 0.01%, it may be difficult to obtain a stable cosmetic. When the blending quantity exceeds 10%, it may not be preferable as a cosmetic in terms of stability during long term storage at high temperatures and the feeling in use may be poor.

The oil-in-water emulsified cosmetic according to the present invention can be produced by mixing and dispersing the cosmetic raw material into water or an aqueous phase component, adding the oil phase component and other components, stirring the mixture and applying shearing force to emulsify the mixture in a usual method.

In the following, the oil phase components and the aqueous phase components applicable in the present invention will be described.

Oil Phase Component

Examples of the oil phase components include hydrocarbon oils, higher fatty acids, higher alcohols, synthetic esters, silicone oils, liquid fats and oils, solid fats and oils, waxes, and perfumes that are commonly used in cosmetics, quasi-drugs, etc.

Examples of the hydrocarbon oils include isododecane, isohexadecane, isoparaffin, liquid petrolatum, ozocerite, squalane, pristane, paraffin, ceresin, squalene, petrolatum, and microcrystallin wax.

Examples of the higher fatty acids include lauric acid, myristic acid, palmitic acid, stearic acid, behenic acid, oleic acid, undecylenic acid, tall oil, isostearic acid, linolic acid, linoleic acid, eicosapentaenoic acid (EPA), and docosahexaenoic acid (DHA).

Examples of the higher alcohols include straight chain alcohols (for example, lauryl alcohol, cetyl alcohol, stearyl alcohol, behenyl alcohol, myristyl alcohol, oleyl alcohol, and cetostearyl alcohol) and branched chain alcohols (for example, monostearyl glycerin ether (batyl alcohol), 2-decyltetradecynol, lanolin alcohol, cholesterol, phytosterol, hexyl dodecanol, isostearyl alcohol, and octyl dodecanol).

Examples of the synthetic ester oils include octyl octanoate, nonyl nonanoate, cetyl octanoate, isopropyl myristate, octyl dodecyl myristate, isopropyl palmitate, butyl stearate, hexyl laurate, myristyl myristate, decyl oleate, hexyl decyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, n-alkylene glycol monoisostearate, neopentyl glycol dicaprate, tripropylene glycol pivalate, diisostearyl malate, glyceryl di-2-heptylundecanoate, glyceryl diisostearate, trimethylolpropane tri-2-ethyl hexanoate, trimethylolpropane triisostearate, pentaerythritol tetra-2-ethylhexanoate, glycerin tri-2- ethylhexanoate, glyceryl trioctanoate, glycerin triisopalmitate, trimethylolpropane triisostearate, cetyl 2-ethyl hexanoate, 2-ethylhexyl palmitate, glycerin trimyristate, tri-2-heptyl undecanoic acid glyceride, castor oil fatty acid methyl ester, oleyl oleate, aceto glyceride, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of the silicone oils include chain polysiloxanes (for example, dimethylpolysiloxane, methylphenyl polysiloxane, and diphenyl polysiloxane), ring polysiloxanes (for example, octamethylcyclotetrasiloxane, decamethyl cyclopenta siloxane, and dodecamethyl cyclohexa siloxane), silicone resins forming a three-dimensional network structure, silicone rubbers, various modified polysiloxanes (amino-modified polysiloxane, polyether-modified polysiloxane, alkyl-modified polysiloxane, and fluorine-modified polysiloxane), and acryl silicones.

Examples of the liquid fats and oils include avocado oil, tsubaki oil, turtle fatty acid, macadamia nut oil, corn oil, mink oil, olive oil, rapeseed oil, egg yolk oil, sesame oil, persic oil, wheat germ oil, sasanquan oil, castor oil, linseed oil, safflower oil, cotton seed oil, *perilla* oil, soybean oil, peanut oil, tea seed oil, Japanese nutmeg oil, rice bran oil, Chinese gimlet oil, Japanese gimlet oil, jojoba oil, germ oil, and triglycerin.

Examples of the solid fats and oils include cacao butter, coconut oil, horse fat, hydrogenated coconut oil, palm oil, beef tallow, mutton tallow, hydrogenated beef tallow, palm kernel oil, lard, beef bone fat, Japanese core wax nucleus oil, hydrogenated oil, neatsfoot oil, Japanese core wax, and hydrogenated castor oil.

Examples of the waxes include beeswax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin ethyl alcohol ether.

Selection of the perfume is not limited in particular; examples include natural perfumes from animals or plants, synthetic perfumes prepared by means of chemical synthesis, and perfume blends thereof. By blending perfume, a cosmetic having a superior durability of fragrance can be obtained.

Specific examples of perfumes include acetivenol, anise aldehyde, anethole, amyl acetate, amyl salicylate, allyl amyl glycolate, allyl caproate, aldehyde C6-20, ambrettolide, ambrettolide, ambroxan, ionone, Iso E Super, eugenol, auranthiol, galaxolide, calone, coumarin, geraniol, geranyl acetate, Sandalore, santalol, sandela, cyclamen aldehyde, cis-3-hexenyl acetate, cis-3-hexenol, citral, citronellyl acetate, citronellol, cineole, dihydromyrcenol, jasmolactone, cinnamic alcohol, cinnamic aldehyde, styralyll acetate, cedryl acetate, cedrol, damascone, damascenone, decalactone, terpinyl acetate, terpineol, tonalid, tonalide, triplal, nerol, bacdanol, vanillin, hydroxycitronellal, phenylethyl acetate, phenylethyl alcohol, hexyl salicylate, vetiveryl acetate, hedione, heliotropin, helional, vertofix, benzyl acetate, benzyl salicylate, benzyl benzoate, pentalide, pentalide, bornyl acetate, myol, musk ketone, methyl anthranilate, methyl dihydrojasmonate, yara yara, lime oxide, linalyl acetate, linarol, limonene, Lyral, lilial, rose oxide, rhodinol, *Angelica* oil, anise oil, *Artemisia vulgaris* oil, basil oil, bay oil, Bergamot oil, calamus oil, camphor oil, *cananga* oil, cardamom oil, *cassia* oil, cedar wood oil, celery oil, chamomile oil, cinnamon oil, clove oil, coriander oil, cumin oil, dill oil, elemi oil, estragon oil, *eucalyptus* oil, fennel oil, fenugreek oil, *galbanum* oil, geranium oil, ginger oil, grapefruit oil, gaiac wood oil, cypress leaf oil, cypress oil, juniper berry oil, lavandin oil, lavender oil, lemon oil, lime oil, mandarin oil, ziram oil, *mimosa* oil, peppermint oil, spearmint oil, mill oil, myrtle oil, nutmeg oil, oakmoss oil, olibanum oil, opoponax oil, orange oil, parsley oil, patchouli oil, pepper oil, *perilla* oil, petit grain oil, neroli oil, orange flower, oil, pimento oil, all spice oil, pine oil, rose oil, rosemary oil, clary sage oil, sage oil, sandalwood oil, *styrax* oil, taget oil, thyme oil, tuberose oil, valerian oil, vetiver oil, violet leaf oil, wintergreen oil, wormwood oil, ilan ilan oil, yuzu oil, cassie absolute, genet absolute, hyacinth absolute, immortelle absolute, jasmine absolute, jonquil absolute, narcis absolute, rose absolute, violet leaf absolute, and benzoin.

Water, water soluble alcohols, thickeners, etc. commonly used in cosmetics, quasi-drugs, etc. can be blended as aqueous phase components; in addition, appropriate amounts of moisturizers, chelating agents, preservatives, pigments, etc. can also be blended in as desired.

The selection of water contained in the oil-in-water emulsified cosmetic of the present invention is not limited in particular; specific examples include purified water, ion-exchanged water, and tap water.

Examples of water soluble alcohols include lower alcohols, polyhydric alcohols, polyhydric alcohol polymers, dihydric alcohol alkyl ethers, dihydric alcohol ether esters, glycerin monoalkyl ethers, sugar alcohols, monosaccharides, oligosaccharides, polysaccharides, and derivatives thereof.

Examples of lower alcohols include ethanol (may be abbreviated as EtOH), propanol, isopropanol, isobutyl alcohol, and t-butyl alcohol.

Examples of polyhydric alcohols include: dihydric alcohols (for example, dipropylene glycol, 1,3-butylene glycol, ethylene glycol, trimethylene glycol, 1,2-butylene glycol, tetramethylene glycol, 2,3-butylene glycol, pentamethylene glycol, 2-butene-1,4-diol, hexylene glycol, and octylene glycol); trihydric alcohols (for example, glycerin and trimethylolpropane); tetrahydric alcohols (for example, diglycerin and pentaerythritol such as 1,2,6-hexanetriol); pentahydric alcohols (for example, xylitol and triglycerin); hexahydric alcohols (for example, sorbitol and mannitol); polyhydric alcohol polymers (for example, diethylene glycol, dipropylene glycol, triethylene glycol, polypropylene glycol, tetraethylene glycol, diglycerin, triglycerin, tetraglycerin, and polyglycerin); dihydric alcohol alkylethers (for example, ethylene glycol monomethyl ether, ethylene glycol monoethyl ether, ethylene glycol monobutyl ether, ethylene glycol monophenyl ether, ethylene glycol monohexyl ether, ethylene glycol mono 2-methyl hexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether, diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); dihydric alcohol ether esters (for example, ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate); glycerin mono alkyl ethers (for example, xylyl alcohol, selachyl alcohol, and batyl alcohol); sugar alcohols (for example, maltotriose, mannitol, sucrose, erythritol, glucose, fructose, starch amylolysis sugar, maltose, and alcohol prepared by the reduction of starch amylolysis sugar); glysolid; tetrahydro furfuryl alcohol; POE-tetrahydro furfuryl alcohol; POP-butyl ether; POP/POE-butyl ether; tripolyoxypropylene glycerin ether; POP-glycerin ether; POP-glycerin ether phosphoric acid; POP/POE-pentane erythritol ether; and polyglycerin.

Examples of monosaccharides include: trioses (for example, D-glyceryl aldehyde and dihydroxyacetone); tetroses (for example, D-etythrose, D-erythrulose, D-threose, and erythritol); pentoses (for example, L-arabinose, D-xylose, L-lyxose, D-arabinose, D-ribose, D-ribulose, D-xylulose, and L-xylulose); hexoses (for example, D-glucose, D-talose, D-psicose, D-galactose, D-fructose, L-galactose, L-mannose, and D-tagatose); heptoses (for example, aldoheptose and heprose); octoses (for example, octurose); deoxysugars (for example, 2-deoxy-D-ribose, 6-deoxy-L-galactose, and 6-deoxy-L-mannose); amino sugars (for example, D-glucosamine, D-galactosamine, sialic acid, amino uronic acid, and muramic acid); and uronic acid (for example, D-glucuronic acid, D-mannuronic acid, L-guluronic acid, D-galacturonic acid, and L-iduronic acid).

Examples of oligosaccharides include sucrose, gentianose, umbelliferose, lactose, planteose, isolignoses, α,α-trehalose, raffinose, lignoses, umbilicine, stachyose and verbascoses.

Examples of polysaccharides include cellulose, quince seed, starch, galactan, dermatan sulfate, glycogen, gum arabic, heparan sulfate, traganth gum, keratan sulfate, chondroitin, xanthan gum, guar gum, dextran, kerato sulfate, locust bean gum, and succinoglucan.

Examples of polyols include polyoxyethylene methyl glucoside (Glucam E-10) and polyoxypropylene methyl glucoside (Glucam P-10).

Examples of thickeners include: gum arabic, carrageenan, karaya gum, gum tragacanth, carob gum, quince seed (*Cydonia oblonga*), casein, dextrin, gelatin, sodium pectate, sodium arginate, methyl cellulose, ethyl cellulose, CMC, hydroxy ethyl cellulose, hydroxypropyl cellulose, PVA, PVM, PVP, sodium polyacrylate, carboxy vinyl polymer, locust bean gum, guar gum, tamarind gum, cellulose dialkyl dimethylammonium sulfate, xanthan gum, aluminum magnesium silicate, bentonite, hectorite, AlMg silicate (beagum), laponite, and silicic acid anhydride.

Examples of natural water-soluble polymers include: plant-type polymers (for example, gum arabic, gum tragacanth, galactan, guar gum, carob gum, karaya gum, carrageenan, pectin, agar, quince seed (*Cydonia oblonga*), algae colloids (brown algae extract), starches (rice, corn, potato, and wheat), and glycyrrhizic acid); microorganism-type polymers (for example, xanthan gum, dextran, succinoglucan, and pullulan); and animal-type polymers (for example, collagen, casein, albumin, and gelatin).

Examples of semisynthetic water-soluble polymers include: starch-type polymers (for example, carboxymethyl starch and methylhydroxypropyl starch); cellulosic polymers (for example, methyl cellulose, ethyl cellulose, methylhydroxypropyl cellulose, hydroxyethyl cellulose, cellulose sodium sulfate, hydroxypropyl cellulose, carboxymetyl-cellulose, sodium carboxymethyl cellulose, crystal cellulose, and cellulose powder); and alginic acid-type polymers (for example, sodium alginate and propylene glycol alginate).

Examples of synthetic water-soluble polymers include: vinyl polymers (for example, polyvinyl alcohol, polyvinyl methyl ether, polyvinylpyrrolidone, carboxy vinyl polymer); polyoxyethylene-type polymers (for example, polyethylene glycol 20,000, 40,000, 60,000, etc.); acrylic polymers (for example, sodium polyacrylate, polyethylacrylate, and polyacrylamide); polyethyleneimine; and cationic polymers.

Examples of moisturizers include chondroitin sulfate, hyaluronic acid, mucoitin sulfuric acid, charonic acid, atelocollagen, cholesteryl-12-hydroxy stearate, sodium lactate, bile salt, dl-pyrrolidone carboxylic acid salt, short chain soluble collagen, diglycerin (EO)PO adduct, chestnut rose fruit extract, yarrow extract, and sweet clover extract.

Examples of sequestering agents include 1-hydroxy ethane-1,1-diphosphonic acid, 1-hydroxy ethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, and trisodium ethylenediaminehydroxyethyl triacetate.

Examples of amino acids include neutral amino acids (for example, threonine and cysteine) and basic amino acids (for example, hydroxylysine). Examples of the amino acid derivatives include sodium acyl sarcosinate (sodium N-lauroyl sarcosinate), acyl glutamate, sodium acyl β-alanine, and glutathione.

Examples of pH adjustment agents include buffers such as lactic acid-sodium lactate, citric acid-sodium citrate, and succinic acid-sodium succinate.

The blending quantity of the oil phase components and the water phase components in the oil-in-water emulsified cosmetic according to the present invention are not limited in particular. By using the cosmetic raw material as an emulsifier, an oil-in-water emulsified cosmetic with a wide range of oil phase components/water phase components ratios, ranging from embodiments having smaller oil phase components/water phase components ratios, i.e., smaller blending ratios of the oil phase components (essences, emulsions, etc.) to embodiments having larger blending ratios of the oil phase components (cleansing creams, sunscreens, hair creams, etc.) can be obtained.

Other components normally used in external preparations such as cosmetics and quasi-drugs can be blended as necessary in the cosmetic according to the present invention as long as the effect of the present invention is not adversely affected; examples of such components include ultraviolet absorbents, powders, organic amines, polymer emulsions, vitamins, and antioxidants.

Examples of water soluble ultraviolet absorbents include benzophenone-type ultraviolet absorbents such as 2,4-dihydroxybenzophenone, 2,2'-dihydroxy-4-methoxy benzophenone, 2,2'-dihydroxy-4,4'-dimethoxybenzophenone, 2,2',4,4'-tetrahydroxy benzophenone, 2-hydroxy-4-methoxy benzophenone, 2-hydroxy-4-methoxy-4'-methylbenzophenone, 2-hydroxy-4-methoxy benzophenone-5-sulfonate, 4-phenyl benzophenone, 2-ethylhexyl-4'-phenyl-benzophenone-2-carboxylate, 2-hydroxy-4-n-octoxy benzophenone, and 4-hydroxy-3-carboxy benzophenone, the benzimidazole-type ultraviolet absorbent such as phenylbenzimidazole-5-sulfonic acid and salts thereof and phenylene-bis-benzimidazole-tetrasulfonic acid and salts thereof, as well as 3-(4'-methylbenzylidene)-d,l-camphor, 3-benzylidene-d,l-camphor, urocanic acid, and urocanic acid ethyl ester.

Examples of the oil soluble ultraviolet absorbents include: benzoic acid-type ultraviolet light absorbents such as paraminobenzoic acid (PABA), PABA monoglycerin ester, N, N-dipropoxy PABA ethyl ester, N, N-diethoxy PABA ethyl ester, N,N-dimethyl PABA ethyl ester, and N, N-dimethyl PABA butyl ester; anthranilic acid-type ultraviolet light absorbents such as homo menthyl-N-acetyl anthranilate; salicylic acid-type ultraviolet light absorbents such as amyl salicylate, menthyl salicylate, homo menthyl salicylate, octyl salicylate, phenyl salicylate, benzyl salicylate, and p-isopropanol phenyl salicylate; cinnamic acid-type ultraviolet absorbents such as octyl cinnamate, ethyl-4-isopropyl cinnamate, methyl-2,5-diisopropyl cinnamate, ethyl-2,4-diisopropyl cinnamate, methyl-2,4-di isopropyl cinnamate, propyl-p-methoxy cinnamate, isopropyl-p-methoxy cinnamate, isoamyl-p-methoxy cinnamate, octyl-p-methoxy cinnamate, 2-ethylhexyl-p-methoxy cinnamate, 2-ethoxy-ethyl-p-methoxy cinnamate, cyclohexyl-p-methoxy cinnamate, ethyl-α-cyano-.beta.-phenyl cinnamate, 2-ethylhexyl-α,α-cyano-β-phenyl cinnamate, glyceryl mono-2-ethyl hexanoyl-diparamethoxy cinnamate, and 3-methyl-4-[methylbis(trimethylsiloxy)silyl]butyl 3,4,5-trimethoxy cinnamate; 2-phenyl-5-methyl benzoxazole, 2,2'-hydroxy-5-methylphenyl benzotriazol, 2-(2'-hydroxy-5'-t-octylphenyl) benzotriazol, 2-(2'-hydroxy-5'-methylphenyl)benzotriazol, dibenzaladine, dianisoylmethane, 4-methoxy-4'-t-butyl dibenzoyl-methane, and 5-(3,3'-dimethyl-2-norbornylidene)-3-pentane-2-one, and octocrylene.

Examples of powder components include inorganic powders (for example, talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstic acid metal salt, magnesium, silica, zeolite, barium sulfate, firing calcium sulfate (calcined gypsum), calcium phosphate, fluorine-apatite, hydroxy apatite, ceramic powder, metallic soaps (for example, zinc myristate, calcium palmitate, and aluminum stearate), and boron nitride); organic powders (for example, polyamide resin powder (nylon powder), polyethylene powder, poly-methyl methacrylate powder, polystyrene powder, powders of the copolymer resin of styrene and acrylic acid, benzoguanamine resin powder, polytetrafluoroethylene powder, and cellulose powder); inorganic white pigments (for example, titanium dioxide and zinc oxide); inorganic red pigments (for example, iron oxide (red iron oxide) and iron titanate); inorganic brown pigments (for example, .gamma.-iron oxide); inorganic yellow pigments (for example, yellow iron oxide and loess); inorganic black pigments (for example, black iron oxide and low oxides of titanium); inorganic purple pigments (for example, mango violet, cobalt violet); inorganic green pigments (for example, chromium oxide, chromium hydroxide, and cobalt titanate); inorganic blue pigments (for example, ultramarine blue and Berlin blue); pearl pigment (for example, titanium oxide coated mica, titanium oxide coated bismuth oxychloride, titanium oxide coated talc, coloration titanium oxide coated mica, bismuth oxychloride, fish scale flakes); metal powder pigments (for example, aluminum powder, copper powder); organic pigments such as zirconium, barium or aluminum rake (for example, organic pigments such as red 201, red 202, red 204, red 205, red 220, red 226, red 228, red 405, orange 203, orange 204, yellow 205, yellow 401 and blue 404, as well as red 3, red 104, red 106, red 227, red 230, red 401, red 505, orange 205, yellow 4, yellow 5, yellow 202, yellow 203, green 3 and blue 1); and natural colors (for example, chlorophyll and β-carotene).

As described above, it is known that some types of inorganic powders can act as Pickering emulsifiers and, in such case, the surfaces of the emulsified particles need to be completely coated with inorganic powders. The emulsified particles whose surfaces are completely coated with inorganic powders are those that can be obtained by optimizing all of the conditions for formulations and stirring under the presence of a large amount of inorganic powders. Thus, inorganic powders do not act as Pickering emulsifiers in most cases when they are blended in cosmetics in general.

Examples of organic amines include monoethanolamine, diethanolamine, triethanolamine, morpholine, tetrakis(2-hydroxypropyl)ethylenediamine, triisopropanolamine, 2-amino-2-methyl-1,3-propanediol, and 2-amino-2-methyl-1-propanol.

Examples of polymer emulsions include acrylic resin emulsions, ethyl polyacrylate emulsions, acryl resin liquids, polyacrylic alkyl ester emulsions, polyvinyl acetate resin emulsions, and natural rubber latex.

Examples of vitamins include vitamins A, B1, B2, B6, C and E as well as their derivatives, pantothenic acid and its derivatives, and biotin.

Examples of antioxidants include tocopherols, dibutyl hydroxytoluene, butyl hydroxyanisole, and gallic acid ester.

Examples of antioxidation assistants include phosphoric acid, citric acid, ascorbic acid, maleic acid, malonic acid, succinic acid, fumaric acid, cephalin, hexametaphosphate, phytic acid, and ethylene diamine tetraacetic acid.

Examples of other possible components include antiseptics (methylparaben, ethylparaben, butylparaben, and phenoxyethanol); antiphlogistic agents (for example, glycyrrhizic acid derivatives, glycyrrhetinic acid derivatives, salicylic acid derivatives, hinokitiol, zinc oxide, and allantoin); whitening agents (for example, placenta extract, creeping saxifrage extract, and arbutin); various extracts (for example, Phellodendri Cortex, goldthread, lithospermum root, *Paeonia lactiflora*, *Swertia japonica*, Birch, sage, loquat, carrot, aloe, Malva *sylvestris*, Iris, grape, *Coix* mayuen, sponge gourd, lily, saffron, Cnidium *officinale*, sheng jiang, *Hypericum erectum*, Ononis, garlic, Guinea pepper, chen pi, *Ligusticum* acutilobum, and seaweed), activators (royal jelly, photosensitive substances, and cholesterol derivatives); blood circulation promoting agents (for example, nonyl acid valenyl amide, nicotinic acid benzyl esters, nicotinic acid β-butoxy ethyl esters, capsaicin, gingeron, cantharis tincture, Ichthammol, tannic acid, α-borneol, tocopherol nicotinate, inositol hexanicotinate, cyclandelate, cinnarizine, tolazoline, acetylcholine, verapamil, cepharanthine, and γ-orizanol); anti-seborrhea agents (for example, sulfur and thiantol); and anti-inflammatory agents (for example, tranexamic acid, thiotaurine, and hypotaurine).

Also, not as the emulsifying agent but for the purpose of controlling tactile sensations during use, controlling drug permeation and such, or improving washability when blended into washing agents for skin and hair, surfactants can be blended into the aqueous phase or oil phase of the oil-in-water emulsified cosmetic of the present invention as long as the effect of the present invention is not adversely affected (for example, 2% by mass, more preferably 1% by mass, and further preferably 0.5% by mass or less).

An ampholytic surfactant has at least one cationic functional group and one anionic functional group, is cationic when the solution is acidic and anionic when the solution is alkaline, and assumes characteristics similar to a nonionic surfactant around the isoelectric point.

Ampholytic surfactants are classified, based on the type of the anionic group, into the carboxylic acid type, the sulfuric ester type, the sulfonic acid type, and the phosphoric ester type. For the present invention, the carboxylic acid type, the sulfuric ester type, and the sulfonic acid type are preferable. The carboxylic acid type is further classified into the amino acid type and the betaine type. Particularly preferable is the betaine type.

Specific examples include: imidazoline type ampholytic surfactants (for example, 2-undecyl-N,N,N-(hydroxyethyl carboxymethyl)-2-imidazoline sodium salt and 2-cocoyl-2-imidazolinium hydroxide-1-carboxyethyloxy 2 sodium salt); and betaine type surfactants (for example, 2-heptadecyl-N-carboxymethyl-N-hydroxyethyl imidazolinium betaine, lauryldimethylaminoacetic acid betaine, alkyl betaine, amide betaine, and sulfobetaine).

Examples of cationic surfactants include quaternary ammonium salts such as cetyltrimethylammonium chloride, stearyltrimethylammonium chloride, behenyltrimehylammonium chloride, behenyldimethylhydroxyethylammonium chloride, stearyldimethylbenzylammonium chloride, and cetyltrimethylammonium methyl sulfate. Other examples include amide amine compounds such as stearic diethylaminoethylamide, stearic dimethylaminoethylamide, palmitic diethylaminoethylamide, palmitic dimethylaminoethylamide, myristic diethylaminoethylamide, myristic dimethylaminoethylamide, behenic diethylaminoethylamide, behenic dimethylaminoethylamide, stearic di ethylaminopropylamide, stearic dimethylaminopropylamide, palmitic diethylaminopropylamide, palmitic dimethylaminopropylamide, myristic diethylaminopropylamide, myristic dimethylaminopropylamide, behenic diethylaminopropylamide, and behenic dimethylaminopropylamide.

Anionic surfactants are classified into the carboxylate type such as fatty acid soaps, N-acyl glutamates, and alkyl ether acetates, the sulfonic acid type such as α-olefin sulfonates, alkane sulfonates, and alkylbenzene sulfonates, the sulfuric ester type such as higher alcohol sulfuric ester salts, and phosphoric ester salts. Preferable are the carboxylate type, the sulfonic acid type, and the sulfuric ester salt type; particularly preferable is the sulfuric ester salt type.

Specific examples include fatty acid soaps (for example, sodium laurate and sodium palmitate); higher alkyl sulfuric acid ester salts (for example, sodium lauryl sulfate and potassium lauryl sulfate); alkyl ether sulfuric acid ester salts (for example, POE-triethanolamine lauryl sulfate and sodium POE-lauryl sulfate); N-acyl sarcosinic acids (for example, sodium lauroyl sarcosinate); higher fatty acid amide sulfonic acid salts (for example, sodium N-myristoyl N-methyl taurate, sodium cocoyl methyl taurate, and sodium laurylmethyl taurate); phosphoric ester salts (for example, sodium POE-oleyl ether phosphate and POE stearyl ether phosphoric acid); sulfosuccinates (for example sodium di-2-ethylhexylsulfosuccinate, sodium monolauroyl monoethanol amide polyoxyethylene sulfosuccinate, and sodium lauryl polypropylene glycol sulfosuccinate); alkyl benzene sulfonates (for example, sodium linear dodecyl benzene sulfonate, triethanolamine linear dodecyl benzene sulfonate, and linear dodecyl benzene sulfonic acid); higher fatty acid ester sulfates (for example, hydrogenated coconut oil aliphatic acid glycerin sodium sulfate); N-acyl glutamates (for example, mono sodium N-lauroylglutamate, disodium N-stearoylglutamate, and sodium N-myristoyl-L-glutamate); sulfated oils (for example, turkey red oil); POE-alkyl ether carboxylic acid; POE-alkyl aryl ether carboxylate; α-olefin sulfonate; higher fatty acid ester sulfonates; sec-alcohol sulfates; higher fatty acid alkyl amide sulfates; sodium lauroyl monoethanolamine succinates; ditriethanolamine N-palmitoylaspartate; and sodium caseinate.

A nonionic surfactant is a surfactant that is not ionized to assume an electric charge in an aqueous solution. For the hydrophobic group, a type that uses alkyls and a type that uses dimethyl silicone are known among others. Specific examples of the former include glycerol fatty acid esters, ethylene oxide derivatives of glycerol fatty acid esters, polyglycerol fatty acid esters, propylene glycol fatty acid esters, ethylene oxide derivatives of propylene glycol fatty acid esters, polyethylene glycol fatty acid esters, polyethylene glycol alkyl ethers, polyethylene glycol alkyl phenyl ethers, polyethylene glycol castor oil derivatives, and polyethylene glycol hydrogenated castor oil derivatives. Examples of the latter include polyether-modified silicone and polyglycerin-modified silicone. Preferable is the type that uses alkyl for the hydrophobic group.

Specific examples of lipophilic nonionic surfactants include sorbitan fatty acid esters (for example, sorbitan mono oleate, sorbitan mono isostearate, sorbitan mono laurate, sorbitan mono palmitate, sorbitan mono stearate, sorbitan sesquioleate, sorbitan trioleate, diglycerol sorbitan penta-2-ethylhexylate, diglycerol sorbitan tetra-2-ethylhexylate); glycerin polyglycerin aliphatic acids (for example, mono cottonseed oil fatty acid glycerin, glyceryl monoerucate, glycerin sesquioleate, glyceryl monostearate, α, α'-glycerin oleate pyroglutamate, monostearate glycerin malic acid); propylene glycol fatty acid esters (for example, propylene glycol monostearate); hydrogenated castor oil derivatives; and glycerin alkylethers.

Examples of hydrophilic nonionic surfactants include POE-sorbitan fatty acid esters (for example, POE-sorbitan monooleate, POE-sorbitan monostearate, POE-sorbitan monooleate, and POE-sorbitan tetraoleate); POE sorbitol fatty acid esters (for example, POE sorbitol monolaurate, POE-sorbitol monooleate, POE-sorbitolpentaoleate, and POE-sorbitol monostearate); POE-glycerin fatty acid esters (for example, POE-monooleates such as POE-glycerin monostearate, POE-glycerin monoisostearate, and POE-glycerin triisostearate); POE-fatty acid esters (for example, POE-distearate, POE-monodioleate, and ethylene glycol distearate); POE-alkylethers (for example, POE-lauryl ether, POE-oleyl ether, POE-stearyl ether, POE-behenyl ether, POE-2-octyl dodecyl ether, and POE-cholestanol ether); pluaronics (for example, pluaronic); POE.cndot. POP-alkylethers (for example, POE.cndot. POP-cetyl ether, POE.cndot. POP-2-decyl tetradecyl ether, POE.cndot. POP-monobutyl ether, POE.cndot. POP-lanolin hydrate, and POE.cndot. POP-glycerin ether); tetra POE.cndot. tetra POP-ethylenediamino condensates (for example, tetronic); POE-castor oil hydrogenated castor oil derivatives (for example, POE-castor oil, POE-hydrogenated castor oil, POE-hydrogenated castor oil monoisostearate, POE-hydrogenated castor oil triisostearate, POE-hydrogenated castor oil monopyroglutamic monoisostearic diester, and POE-hydrogenated castor oil maleic acid); POE-beeswax-lanolin derivatives (for example, POE-sorbitol beeswax); alkanol amides (for example, palm oil fatty acid diethanol amide, laurate monoethanolamide, and fatty acid isopropanol amide); POE-propylene glycol fatty acid esters; POE-alkylamines; POE-fatty acid amides; sucrose fatty acid esters; alkyl ethoxydimethylamine oxides; and trioleyl phosphoric acid.

The cosmetic raw material of the present invention can be used as a clouding agent.

White turbidity, an appearance feature, in cosmetics (especially cosmetic lotions) is strongly supported by some consumers as it evokes moisturizing feeling, moist feeling, full-bodied feeling or the like. White cloudy cosmetics are generally produced by dispersing ethanol of which surfactants and oil are dissolved to an aqueous phase; however, the adjustment of the surfactant and oil balance was difficult and obtaining a white cloudy cosmetic that is excellent in stability over time was not easy.

White turbidity can visually be confirmed by blending only 0.01% (converted value of the pure content of the core-corona type microparticles) of the cosmetic raw material according to the present invention into water. By blending 0.01 to 0.1% thereof, the white turbidity with the L value (brightness) of 1 to 80, measured with a Macbeth color difference meter, can be obtained.

A white cloudy cosmetic in the present invention means a cosmetic whose appearance can be visually recognized to be turbid. L value is preferably 1 to 90.

To produce the white cloudy cosmetic, the clouding agent of the present invention can be used by mixing and dispersing into water (or an aqueous phase of which aqueous components are dissolved) by a usual method in a producing process of an ordinary cosmetic. The blending amount, as a pure content of the core-corona type microparticles, is 0.01 to 10% by mass, more preferably 0.05 to 2% by mass, and further more preferably 0.05 to 1% by mass relative to the total amount of the cosmetic. When the blending amount is less than 0.01%, white turbidity may not be sufficient. When the blending amount exceeds 10% by mass, it may not be preferable in terms of stability during long term storage at high temperatures and the feeling in use may be poor.

The oil-in-water emulsified cosmetic and the white cloudy cosmetic are preferable as skin cosmetics and skin external agents.

EXAMPLES

The present invention will be described with reference to the following examples, but the present invention is not limited thereto. The blending amounts are expressed with "% by mass" unless otherwise specified. EtOH, DPG and BG described in the tables are abbreviations for ethanol, dipropylene glycol and 1,3-butylene glycol, respectively.

Example 1: Production Example of a Core-Corona Type Microparticle Dispersion Macro monomer and hydrophobic monomer described in Table 1 were radically polymerized under polymerization conditions shown in Tables 1 and 2 in accordance with the following production method (Technique 1). The appearance of the obtained copolymer dispersion was evaluated visually, and the sizes of particles and the degree of dispersion of the copolymers were evaluated in accordance with Technique 2. Results are shown in Table 3.

<Technique 1: Production Method of a Core-Corona Type Microparticle>

Polyethyleneoxide macro monomer and hydrophobic monomer were added into 90 g of water-alcohol mixed solvent in a three-neck flask equipped with a reflux tube and a nitrogen feeding tube. After sufficient dissolution or dispersion, dissolved oxygen was removed by nitrogen substitution for 20 minutes. Then, 1 mol % of the polymerization initiator, 2,2'-azobis(2-methylpropionamidine) dihydrochloride, with respect to the total amount of monomers, was dissolved in a small amount of water and added, and further dissolution or dispersion was carried out. The uniformly dissolved or dispersed polymerization solution was put through nitrogen substitution for 20 minutes to remove dissolved oxygen, followed by 8 hours of polymerization with stirring by means of a magnetic stirrer while the temperature was maintained at 65 to 70° C. in an oil bath. After the completion of polymerization, the polymer solution was returned to room temperature; thus a core-corona type microparticle dispersion was obtained.

As a polyethylene oxide macro-monomer, Blemmer PME-4000 (produced by NOF CORPORATION) was used. As hydrophobic monomers, methyl methacrylate (MMA), butyl methacrylate (n-BMA), t-butylacrylamide (t-BAA), N,N-dimethylacrylamide (DMAA) and N-[3-(dimethylamino)propyl]acrylamide (DMAPA) were used.

<Technique 2: Method for Measuring the Particle Size and the Degree of Dispersion>

The particle size of copolymers was measured using a Zetasizer manufactured by Malvern Instruments Ltd. Measurement samples of the microparticle dispersion liquid with the microparticle concentration of about 0.1% were prepared by dilution with water. After removing dust with a 0.45 μm filter, the scattering intensity at 25° C. was measured at the scattering angle of 173° (back-scattered light), the average particle size and the degree of dispersion were calculated with analysis software installed on the measurement apparatus. The particle size was analyzed by the cumulant analysis method. The degree of dispersion is a normalized value of the second-order cumulant value obtained by the cumulant analysis. The degree of dispersion is a commonly used parameter, and the automatic analysis is possible by using a commercial dynamic light scattering measurement apparatus. For the viscosity of the solvent, which was necessary for the particle size analysis, the viscosity of pure water at 25° C., i.e., 0.89 mPa·s, was used.

TABLE 1

| | Macromonomer | | Hydrophobic monomer | | | | | Polymerization solvent | | |
|---|---|---|---|---|---|---|---|---|---|---|
| | Methoxy PEG-4000 Formula (1) | Methoxy PEG-1000 | MMA Formula (2) | n-BMA Formula (2) | t-BAA Formula (3) | DMAA Formula (3) | DMAPA Formula (3) | Water | Alcohol | Amounts of alcohol |
| Production example 1 | 4.07 | | 2.45 | 3.48 | | | | 54 | EtOH | 36 |
| Production example 2 | 3.95 | | | | 6.05 | | | 73.8 | EtOH | 16.2 |

TABLE 1-continued

| | Macromonomer | | Hydrophobic monomer | | | | | Polymerization solvent | | |
|---|---|---|---|---|---|---|---|---|---|---|
| | Methoxy PEG-4000 Formula (1) | Methoxy PEG-1000 | MMA Formula (2) | n-BMA Formula (2) | t-BAA Formula (3) | DMAA Formula (3) | DMAPA Formula (3) | Water | Alcohol | Amounts of alcohol |
| Production example 3 | 3.84 | | | | 4.71 | | 1.45 | 73.8 | EtOH | 16.2 |
| Production example 4 | 3.89 | | | | 4.77 | 0.23 | 1.10 | 73.8 | EtOH | 16.2 |
| Production example 5 | 3.90 | | 0.09 | | 4.67 | 0.23 | 1.10 | 73.8 | EtOH | 16.2 |
| Production example 6 | 4.06 | | 2.40 | 3.41 | 0.06 | | 0.08 | 54 | EtOH | 36 |
| Production example 7 | 2.46 | | 0.30 | | 6.03 | 0.29 | 0.93 | 70.2 | EtOH | 19.8 |
| Production example 8 | 2.46 | | 0.30 | | 6.03 | 0.29 | 0.93 | 58.5 | DPG | 31.5 |
| Production example 9 | | 1.59 | 2.07 | | 5.26 | | 1.08 | 58.5 | BG | 31.5 |
| Production example 10 | 3.03 | | 0.27 | | 5.57 | 0.27 | 0.86 | 70.2 | EtOH | 19.8 |

※All units of the values in Table 4 are gram.

TABLE 2

| | (A) Macromonomer/hydrophobic monomer ratio (mole ratio) | (B-1) Macromonomer Formula (1) | (B-2) Acrylate derivative monomer Formula (2) | | (B-3) Acrylamide derivative monomer Formula (3) | | | (C) Alcohol | (D) Water/alcohol mixed solvent ratio |
|---|---|---|---|---|---|---|---|---|---|
| Production example 1 | 1/50 | $R_1 = CH_3$<br>n = 90 | $R_2 = CH_3$<br>$R_3 = CH_3$ | $R_2 = CH_3$<br>$R_3 = n$-$C_4H_9$ | | | | EtOH | 60/40 |
| Production example 2 | 1/50 | $R_1 = CH_3$<br>n = 90 | | | $R_4 = H$<br>$R_5 = H$<br>$R_6 = t$-$C_4H_9$ | | | EtOH | 82/18 |
| Production example 3 | 1/50 | $R_1 = CH_3$<br>n = 90 | | | $R_4 = H$<br>$R_5 = H$<br>$R_6 = t$-$C_4H_9$ | $R_4 = H$<br>$R_5 = CH_3$<br>$R_6 = CH_3$ | $R_4 = H$<br>$R_5 = H$<br>$R_6 = C_3H_6$<br>$N(CH_3)_2$ | EtOH | 82/18 |
| Production example 4 | 1/50 | $R_1 = CH_3$<br>n = 90 | | | $R_4 = H$<br>$R_5 = H$<br>$R_6 = t$-$C_4H_9$ | $R_4 = H$<br>$R_5 = CH_3$<br>$R_6 = CH_3$ | $R_4 = H$<br>$R_5 = H$<br>$R_6 = C_3H_6$<br>$N(CH_3)_2$ | EtOH | 82/18 |
| Production example 5 | 1/50 | $R_1 = CH_3$<br>n = 90 | $R_2 = CH_3$<br>$R_3 = CH_3$ | | $R_4 = H$<br>$R_5 = H$<br>$R_6 = t$-$C_4H_9$ | $R_4 = H$<br>$R_5 = CH_3$<br>$R_6 = CH_3$ | $R_4 = H$<br>$R_5 = H$<br>$R_6 = C_3H_6$<br>$N(CH_3)_2$ | EtOH | 82/18 |
| Production example 6 | 1/50 | $R_1 = CH_3$<br>n = 90 | $R_2 = CH_3$<br>$R_3 = CH_3$ | $R_2 = CH_3$<br>$R_3 = n$-$C_4H_9$ | $R_4 = H$<br>$R_5 = H$<br>$R_6 = t$-$C_4H_9$ | | $R_4 = H$<br>$R_5 = H$<br>$R_6 = C_3H_6$<br>$N(CH_3)_2$ | EtOH | 60/40 |
| Production example 7 | 1/100 | $R_1 = CH_3$<br>n = 90 | $R_2 = CH_3$<br>$R_3 = CH_3$ | | $R_4 = H$<br>$R_5 = H$<br>$R_6 = t$-$C_4H_9$ | $R_4 = H$<br>$R_5 = CH_3$<br>$R_6 = CH_3$ | $R_4 = H$<br>$R_5 = H$<br>$R_6 = C_3H_6$<br>$N(CH_3)_2$ | EtOH | 78/22 |
| Production example 8 | 1/100 | $R_1 = CH_3$<br>n = 90$_3$ | $R_2 = CH_3$<br>$R_3 = CH_3$ | | $R_4 = H$<br>$R_5 = H$<br>$R_6 = t$-$C_4H_9$ | $R_4 = H$<br>$R_5 = CH_3$<br>$R_6 = CH_3$ | $R_4 = H$<br>$R_5 = H$<br>$R_6 = C_3H_6$<br>$N(CH_3)_2$ | DPG | 65/35 |
| Production example 9 | 1/50 | $R_1 = CH_3$<br>n = 23 | $R_2 = CH_3$<br>$R_3 = CH_3$ | | $R_4 = H$<br>$R_5 = H$<br>$R_6 = t$-$C_4H_9$ | | $R_4 = H$<br>$R_5 = H$<br>$R_6 = C_3H_6$<br>$N(CH_3)_2$ | BG | 65/35 |
| Production example 10 | 1/75 | $R_1 = CH_3$<br>n = 90 | $R_2 = CH_3$<br>$R_3 = CH_3$ | | $R_4 = H$<br>$R_5 = H$<br>$R_6 = t$-$C_4H_9$ | $R_4 = H$<br>$R_5 = CH_3$<br>$R_6 = CH_3$ | $R_4 = H$<br>$R_5 = H$<br>$R_6 = C_3H_6$<br>$N(CH_3)_2$ | EtOH | 78/22 |

TABLE 3

| Production Example | Appearance | Core-corona type microparticle concentration (wt %) | Alcohol type · alcohol concentration (wt %) | Water concentration (wt %) | Particle size (nm) | Degree of dispersion |
|---|---|---|---|---|---|---|
| Production example 1 | white cloudy liquid | 10 | Ethanol · 36 | 90 | 187.0 | 0.017 |
| Production example 2 | white cloudy liquid | 10 | Ethanol · 16.2 | 90 | 153.6 | 0.019 |
| Production example 3 | white cloudy liquid | 10 | Ethanol · 16.2 | 90 | 191.2 | 0.01 |
| Production example 4 | white cloudy liquid | 10 | Ethanol · 16.2 | 90 | 167.2 | 0.002 |
| Production example 5 | white cloudy liquid | 10 | Ethanol · 16.2 | 90 | 166.5 | 0.028 |
| Production example 6 | white cloudy liquid | 10 | Ethanol · 36 | 90 | 210.3 | 0.018 |
| Production example 7 | white cloudy liquid | 10 | Ethanol · 19.8 | 90 | 250.0 | 0.003 |
| Production example 8 | white cloudy liquid | 10 | DPG · 31.5 | 90 | 174.6 | 0.014 |
| Production example 9 | white cloudy liquid | 10 | BG · 31.5 | 90 | 249.9 | 0.149 |
| Production example 10 | white cloudy liquid | 10 | Ethanol · 19.8 | 90 | 197.1 | 0.006 |

As shown in Table 3, in Production Examples 1 to 10 obtained by polymerizing methoxy polyethylene glycol monometalate (macromonomer); and one or two or more hydrophobic monomers selected from methyl methacrylate, butyl methacrylate, t-butylacrylamide, N,N-dimethylacrylamide, and N-[3-(dimethylamino)propyl]acrylamide having a substituent including an alkyl group having 1 to 4 carbon atoms in a water-ethanol mixed solvent (water:ethanol=40 to 60:18 to 82) under the condition that the value of "the feed molar amount of a macromonomer/the feed molar amount of a hydrophobic monomer" became 1:50 to 100, white cloudy solution-like dispersions were obtained, and it was possible to evaluate the particle sizes and the degrees of dispersion. That is, the formation of particulate polymers (core-corona type microparticles) could be confirmed. It was revealed that in the core-corona type microparticles of Production Examples 1 to 10, the particle sizes were 153.6 to 250.0 nm, the degrees of dispersion were 0.002 to 0.149 and the particle sizes were uniform.

Accordingly, it was revealed that the core-corona type microparticles having a uniform size of particles could be obtained by radically polymerizing the polyethylene oxide macromonomer represented by the above following formula (1) and one or two or more hydrophobic monomers selected from the acrylate derivative monomer represented by the above following formula (2) and the acrylamide derivative monomer represented by the above following formula (3), in conformity with the conditions ((A) to (D)):

(A) a molar ratio expressed by a feed molar amount of the polyethylene oxide macromonomer/a feed molar amount of (the acrylate derivative monomer and/or the acrylamide derivative monomer) is 1:10 to 1:250;

(B) the macromonomer represented by the following formula (1) is an acrylic acid derivative or a methacrylic acid derivative having a polyethylene glycol group with 8 to 200 repeating units, the acrylate derivative monomer represented by the following formula (2) is an acrylic acid derivative or a methacrylic acid derivative having a substituent comprising an alkyl group having 1 to 12 carbon atoms, and the acrylamide derivative monomer represented by the following formula (3) is an acrylamide derivative or a methacrylamide derivative having a substituent comprising an alkyl group having 1 to 18 carbon atoms;

(C) a polymerization solvent is a water-alcohol mixed solvent, and the alcohol is one or two or more selected from ethanol, dipropylene glycol, 1,3-butylene glycol and isoprene glycol; and (D) a solvent composition of the water-alcohol mixed solvent is water:alcohol=90 to 10:10 to 90 in a mass ratio at 20° C.

Example 2: Surface Tension Reducing Effect

Effects on oil/aqueous interfacial tension were analyzed with respect to core-corona type microparticles according to the present invention.

A droplet of the core-corona type microparticle dispersion of Production Example 5 was produced in dodecane with a syringe. The dodecane/aqueous interfacial tension at an optional dispersion concentration was measured by a pendant drop method (Automatic contact angle meter DM-501, manufactured by Kyowa Interface Science Co., Ltd.) that can measure interfacial tension values by analyzing the shape of the droplet. The conventional crosslinked core-corona type microparticles ((Acrylates/Methoxy PEG-90 Methacrylate) Crosspolymer) were used as a control. The results are shown in FIG. 1.

In the case of (Acrylates/Methoxy PEG-90 Methacrylate) Crosspolymer, the dodecane/aqueous interfacial tension rapidly decreased when the addition concentration exceeded 0.0001% by weight; but thereafter, the interfacial tension decreased slowly.

In contrast, in the case of the core-corona type microparticles of Production Example 5, the interfacial tension was substantially the same as the aforementioned crosspolymer until the addition concentration was 0.01% by weight; but thereafter, the interfacial tension remarkably decreased as the addition concentration was increased.

Accordingly, it is shown that the core-corona type microparticles according to the present invention are superior in reducing the oil/aqueous interfacial tension compared to conventional crosslinked core-corona type microparticles.

Example 3: Oil-in-Water Emulsified Cosmetic

Next, an example of a cosmetic emulsified by the core-corona type microparticles of the aforementioned production example will be shown. Cosmetics of the formulations described in Table 4 were produced in accordance with Technique 3 and evaluated in accordance with Technique 4. The results are also shown in Table 4.

<Technique 3: Production Method of the Oil-in-Water Emulsified Cosmetic>

Various aqueous phase components such as polyols and thickeners were added to purified water and mixed. The cosmetic raw material according to the present invention was separately dispersed to purified water, added to the mixture, and stirred and mixed. The cosmetic raw material and the aqueous phase components were homogeneously dispersed, to which the oil phase components were added, followed by shear mixing with a homomixer until homogeneous to obtain the oil-in-water emulsified cosmetic.

<Technique 4: Evaluation Method of the Cosmetic>

Evaluation (1): Transparency (White Turbidity)

Samples were measured with a Spectrophotometer V-630 (manufactured by JASCO Corporation) at a wavelength of 600 nm, and the evaluation was carried out based on the visible light transmittance (light path length: 1 cm). Ion-exchanged water was used as the reference.

Evaluation (2-1): Stability (Appearance)

On day after sample preparation, the appearance was visually observed and was evaluated according to the following criteria.
- A: The sample was homogeneous and no oil separation or aggregation was observed.
- B: The sample was mostly homogeneous but slight oil separation or aggregation was observed.
- C: The sample was not homogeneous or significant oil separation or powder aggregation was observed.

Evaluation (2-2): Emulsification stability (Emulsified particles)

Emulsified particles of the sample were observed with an optical microscope.
- A: The sample was homogeneous and no coalescence or aggregation was observed.
- B: The sample was mostly homogeneous but slight coalescence and/or aggregation was observed.
- C: The sample was not homogeneous, or significant coalescence or powder aggregation was observed.

Evaluation (3): Skin Irritation Test

An occlusive patch was applied to the inner upper arm of 10 sensitive skin panelists for 24 hours and the skin was evaluated based on the following criteria.
- 0 . . . No abnormality was observed.
- 1 . . . Slight reddening was observed.
- 2 . . . Reddening was observed.
- 3 . . . Reddening and a papule were observed.

The evaluation criteria of the "skin irritation test" are as follows:
- A: The average of the 10 panelists is 0 or more and less than 0.15.
- B: The average of the 10 panelists is 0.15 or more and less than 0.2.
- C: The average of the 10 panelists is 0.2 or more and less than 0.3.
- D: The average of the 10 panelists is 0.3 or more.

Evaluation (4): Feeling in Use

The feeling in use ("non-stickiness", "full-bodied feeling", and "fast blending"), when the sample was applied on the skin, was evaluated by 10 professional panelists based on the following criteria.
- A: 7 or more panelists answered "good" or "really felt".
- B: 5 or more panelists answered "good" or "really felt".
- C: 3 or more panelists answered "good" or "really felt".
- D: 2 or less panelists answered "good" or "really felt".

Evaluation (5): Stability Over Time

The oil-in-water emulsion cosmetic was visually observed one month after preparation.
- A: The sample was maintaining the emulsified state of the time of preparation.
- B: Some sedimentation/floatation was observed; however, the sample nearly maintained the emulsion state.
- C: Sedimentation/floatation of emulsion particles was observed and coalescence of the particles was also observed.
- D: Sedimentation/floatation/coalescence of emulsion was observed and the oil phase was completely separated.

Evaluation (6): Water-Washability 2 mg/cm$^2$ of a sample was applied to a resin plate, and a UV spectrum in the range of 290 to 400 nm was measured. The plate was stuck on the wall surface of a container with a double-sided tape, and about 20 L water was poured into the container. Then, the plate was exposed to a water stream at 500 rpm for 30 minutes, and thereafter a spectrum was measured again. The rate (percentage) of the integral values of the spectra after washing with water with respect to the integral values of the spectra before washing with water was calculated and defined as a "residual rate of water-washing". When the residual rate of water-washing is 0%, it indicates that the sample is completely washed off

TABLE 4

| | Examples | | | | | | | | | |
|---|---|---|---|---|---|---|---|---|---|---|
| | 1-1 | 1-2 | 1-3 | 1-4 | 1-5 | 1-6 | 1-7 | 1-8 | 1-9 | 1-10 |
| Ion-Exchanged Water | Balance | Balance | Balance | Balance | Balance | Balance | Balance | Balance | Balance | Balance |
| Liquid Paraffin | 10 | 10 | 10 | 10 | 10 | 10 | 10 | 10 | 10 | 10 |
| Tri-2-Ethylhexanoate Glycerin | 10 | 10 | 10 | 10 | 10 | 10 | 10 | 10 | 10 | 10 |
| Dimethylpolysiloxane (6 cs) | 10 | 10 | 10 | 10 | 10 | 10 | 10 | 10 | 10 | 10 |
| Carboxyvinyl Polymer | 0.1 | 0.1 | 0.1 | 0.1 | 0.1 | 0.1 | 0.1 | 0.1 | 0.1 | 0.1 |
| Potassium Hydroxide | 0.06 | 0.06 | 0.06 | 0.06 | 0.06 | 0.06 | 0.06 | 0.06 | 0.06 | 0.06 |
| Core-Corona Particle Dispersion of Production Example 1 | 10 | — | — | — | — | — | — | — | — | — |
| Core-Corona Particle Dispersion of Production Example 2 | — | 10 | — | — | — | — | — | — | — | — |
| Core-Corona Particle Dispersion of Production Example 3 | — | — | 10 | — | — | — | — | — | — | — |
| Core-Corona Particle Dispersion of Production Example 4 | — | — | — | 10 | — | — | — | — | — | — |

TABLE 4-continued

|  | Examples | | | | | | | | | |
|---|---|---|---|---|---|---|---|---|---|---|
|  | 1-1 | 1-2 | 1-3 | 1-4 | 1-5 | 1-6 | 1-7 | 1-8 | 1-9 | 1-10 |
| Core-Corona Particle Dispersion of Production Example 5 | — | — | — | — | 10 | — | — | — | — | — |
| Core-Corona Particle Dispersion of Production Example 6 | — | — | — | — | — | 10 | — | — | — | — |
| Core-Corona Particle Dispersion of Production Example 7 | — | — | — | — | — | — | 10 | — | — | — |
| Core-Corona Particle Dispersion of Production Example 8 | — | — | — | — | — | — | — | 10 | — | — |
| Core-Corona Particle Dispersion of Production Example 9 | — | — | — | — | — | — | — | — | 10 | — |
| Core-Corona Particle Dispersion of Production Example 10 | — | — | — | — | — | — | — | — | — | 10 |
| Total | 100 | 100 | 100 | 100 | 100 | 100 | 100 | 100 | 100 | 100 |
| Evaluation (2-1): Emulsification Stability (Appearance) | A | A | A | B | A | A | A | A | A | A |
| Evaluation (2-2): Emulsification Stability (Particle) | A | A | A | B | A | A | A | A | A | A |
| Evaluation (3): Skin Irritation | A | A | A | B | A | A | A | A | A | A |
| Evaluation (4-1): Dewy Feeling | A | A | A | A | A | A | A | A | A | A |
| Evaluation (4-2): Non-Squeaky Feeling | A | A | A | A | A | A | A | A | A | A |
| Evaluation (4-2): Non-Powdery Feeling | A | A | A | A | A | A | A | A | A | A |
| Evaluation (5): Stability Over Time | A | A | A | B | A | A | A | A | A | A |

*All of the pure content of the core-corona type microparticles in the core-corona particles dispersion in the table is 10% by mass.

As shown in Table 4, all of the oil-in-water emulsified cosmetics of Examples 1-1 to 1-10 were excellent in emulsification stability, less in stickiness and excellent in dewy feeling; and powdery or squeaky feeling was hardly felt.

Accordingly, it is shown that by using the core-corona type microparticles according to the present invention as an emulsifier, an oil-in-water emulsified cosmetic that is excellent in emulsification stability, less in stickiness, excellent in dewy feeling, and less in powdery or squeaky feeling can be obtained.

Example 4: White Cloudy Cosmetic

Subsequently, examples of cosmetics that are clouded by the core-corona type microparticles of the aforementioned production example are shown. Cosmetic lotions of the formulation described in Table 5 were produced by a usual method and were evaluated in accordance with Technique 4. The results are also shown in Table 5.

|  | Examples | | | | | | | | | |
|---|---|---|---|---|---|---|---|---|---|---|
|  | 2-1 | 2-2 | 2-3 | 2-4 | 2-5 | 2-6 | 2-7 | 2-8 | 2-9 | 2-10 |
| Ion-Exchanged Water | Balance | Balance | Balance | Balance | Balance | Balance | Balance | Balance | Balance | Balance |
| Ethanol | 0.64 | 0.84 | 0.84 | 0.84 | 0.84 | 0.64 | 0.8 | 1 | 1 | 0.8 |
| Dipropylene Glycol | 1 | 1 | 1 | 1 | 1 | 1 | 1 | 0.69 | 1 | 1 |
| 1,3-Butylene Glycol | 1 | 1 | 1 | 1 | 1 | 1 | 1 | 1 | 0.69 | 1 |
| Glycerin | 5 | 5 | 5 | 5 | 5 | 5 | 5 | 5 | 5 | 5 |
| Polyethylene glycol 1000 | 1 | 1 | 1 | 1 | 1 | 1 | 1 | 1 | 1 | 1 |
| Paeonia Suffruticosa Root Extract | 0.01 | 0.01 | 0.01 | 0.01 | 0.01 | 0.01 | 0.01 | 0.01 | 0.01 | 0.01 |
| Rubus Idaeus (Raspberry) Fruit Extract | 0.01 | 0.01 | 0.01 | 0.01 | 0.01 | 0.01 | 0.01 | 0.01 | 0.01 | 0.01 |
| Saxifraga Sarmentosa Extract | 0.01 | 0.01 | 0.01 | 0.01 | 0.01 | 0.01 | 0.01 | 0.01 | 0.01 | 0.01 |
| Menthol | 0.02 | 0.02 | 0.02 | 0.02 | 0.02 | 0.02 | 0.02 | 0.02 | 0.02 | 0.02 |
| Citric Acid (Food) | 0.02 | 0.02 | 0.02 | 0.02 | 0.02 | 0.02 | 0.02 | 0.02 | 0.02 | 0.02 |
| Sodium Citrate | 0.08 | 0.08 | 0.08 | 0.08 | 0.08 | 0.08 | 0.08 | 0.08 | 0.08 | 0.08 |
| Sodium Hexametaphosphate | 0.03 | 0.03 | 0.03 | 0.03 | 0.03 | 0.03 | 0.03 | 0.03 | 0.03 | 0.03 |

-continued

|  | Examples | | | | | | | | | |
|---|---|---|---|---|---|---|---|---|---|---|
|  | 2-1 | 2-2 | 2-3 | 2-4 | 2-5 | 2-6 | 2-7 | 2-8 | 2-9 | 2-10 |
| Phenoxy-ethanol | 0.3 | 0.3 | 0.3 | 0.3 | 0.3 | 0.3 | 0.3 | 0.3 | 0.3 | 0.3 |
| Perfume | 0.05 | 0.05 | 0.05 | 0.05 | 0.05 | 0.05 | 0.05 | 0.05 | 0.05 | 0.05 |
| Core-Corona Particle Dispersion of Production Example 1 | 1 | — | — | — | — | — | — | — | — | — |
| Core-Corona Particle Dispersion of Production Example 2 | — | 1 | — | — | — | — | — | — | — | — |
| Core-Corona Particle Dispersion of Production Example 3 | — | — | 1 | — | — | — | — | — | — | — |
| Core-Corona Particle Dispersion of Production Example 4 | — | — | — | 1 | — | — | — | — | — | — |
| Core-Corona Particle Dispersion of Production Example 5 | — | — | — | — | 1 | — | — | — | — | — |
| Core-Corona Particle Dispersion of Production Example 6 | — | — | — | — | — | 1 | — | — | — | — |
| Core-Corona Particle Dispersion of Production Example 7 | — | — | — | — | — | — | 1 | — | — | — |
| Core-Corona Particle Dispersion of Production Example 8 | — | — | — | — | — | — | — | 1 | — | — |
| Core-Corona Particle Dispersion of Production Example 9 | — | — | — | — | — | — | — | — | 1 | — |
| Core-Corona Particle Dispersion of Production Example 10 | — | — | — | — | — | — | — | — | — | 1 |
| Total | 100 | 100 | 100 | 100 | 100 | 100 | 100 | 100 | 100 | 100 |
| Evaluation (1): 600 nm transmission (%) | 49.5 | 66.4 | 57.2 | 68.8 | 65.3 | 40.9 | 21.1 | 58.4 | 31.5 | 45.7 |
| Evaluation (2-1): Stability | A | A | A | A | A | A | A | A | A | A |
| Evaluation (3): Skin initation | A | A | A | A | A | A | A | A | A | A |
| Evaluation (4-1): Non-stickiness | A | A | A | A | A | A | A | A | A | A |

-continued

| | Examples | | | | | | | | | |
|---|---|---|---|---|---|---|---|---|---|---|
| | 2-1 | 2-2 | 2-3 | 2-4 | 2-5 | 2-6 | 2-7 | 2-8 | 2-9 | 2-10 |
| Evaluation (4-2): Full-bodied feeling | B | A | A | A | A | B | A | A | A | A |
| Evaluation (4-3): Fast blending | A | A | B | B | A | A | A | B | A | A |

*All of the pure content of the core-corona type microparticles in the core-corona particles dispersion in the table is 10% by mass.

As shown in Table 5, all of the cosmetics of Examples 2-1 to 2-10 of which the core-corona type microparticles dispersion of Production Examples 1 to 10 were blended exhibited white cloudy appearance ranging from white turbid to blue-white semi-transparent. Moreover, they were excellent in emulsification stability, less in stickiness, had full-bodied feeling and were fast blending; furthermore, powdery or squeaky feeling was hardly felt.

Accordingly, it is shown that the core-corona type microparticles according to the present invention can be used as the clouding agent for cosmetics.

Example 5: Water-Washability

Next, cosmetics of the formulation shown in Table 6 were produced by a usual method, and were evaluated for water-washability in accordance with Technique 4. The results are also shown in Table 6.

TABLE 6

| Formulation | Comparative Example 3-1 | Example 3-1 | Example 3-2 |
|---|---|---|---|
| Alcohol | 7.52 | 6.2 | 6.4 |
| Dipropylene glycol | 6 | 6 | 6 |
| Glycerin | 1 | 1 | 1 |
| (Acrylates/Methoxy PEG-90 Methacrylate) Crosspolymer | 0.7 | — | — |
| Core-Corona Particle Dispersion of Production Example 10 | — | 7 | — |
| Core-Corona Particle Dispersion of Production Example 5 | — | — | 7 |
| (Dimethylacrylamide/Sodium Acryloyldimethyltaurate) Crosspolymer | 0.65 | 0.65 | 0.65 |
| Beheneth-20 | 1 | 1 | 1 |
| Behenyl alcohol | 0.3 | 0.3 | 0.3 |
| Stearyl alcohol | 0.15 | 0.15 | 0.15 |
| Distearyldimonium Chloride | 0.03 | 0.03 | 0.03 |
| Isostearic Acid | 0.8 | 0.8 | 0.8 |
| Diethylhexyl Succinate | 3 | 3 | 3 |
| Diisopropyl Sebacate | 10 | 10 | 10 |
| Triethylhexanoin | 2 | 2 | 2 |
| Isododecane | 12 | 12 | 12 |
| Benzophenone-3 | 1 | 1 | 1 |
| t-butyl Methoxydibenzoyl-methane | 2 | 2 | 2 |
| Ethylhexyl Triazone | 3 | 3 | 3 |
| Bis-Ethylhexyloxyphenol Methoxyphenyl Triazine | 3 | 3 | 3 |
| Titanium Oxide | 5 | 5 | 5 |
| Hydrated Silica | 0.3 | 0.3 | 0.3 |
| EDTA—2Na | 0.05 | 0.05 | 0.05 |

TABLE 6-continued

| Formulation | Comparative Example 3-1 | Example 3-1 | Example 3-2 |
|---|---|---|---|
| Sodium Citrate | 0.02 | 0.02 | 0.02 |
| Citric Acid | 0.05 | 0.05 | 0.05 |
| Ion-exchanged water | Balance | Balance | Balance |
| Total | 100 | 100 | 100 |
| Evaluation (6): Residual rate of water-washability (%) | 84 | 52 | 49 |

*All of the pure content of the core-corona type microparticles in the core-corona particles dispersion in the table is 0.7% by mass.

As shown in Table 6, in the cosmetics of Example 3-1 or 3-2 of which the core-corona type microparticles dispersion of Production Example 10 or 5 were blended, the residual rate after washing with water was 52 or 49 and was sufficiently low. In contrast, in the cosmetic of which the conventional crosslinked core-corona type microparticles ((Acrylates/Methoxy PEG-90 Methacrylate) Crosspolymer) were blended, the residual rate of water-washing was 84% and was high.

Accordingly, it became clear that the cosmetic emulsified by the conventional crosslinked core-corona type microparticles is hardly removed by washing with water, but almost a half of the cosmetic emulsified by the core-corona type microparticles according to the present invention is removed only by washing with water.

We claim:

1. A method for the preparation of an oil-in-water cosmetic, comprising the steps of dispersing uncrosslinked core-corona microparticles into the aqueous phase, adding the oil phase, and applying shearing force for a time sufficient to emulsify the resulting mixture, wherein:

the core-corona microparticles are obtained by radical co-polymerization of a polyethylene oxide macromonomer represented by chemical formula (1)

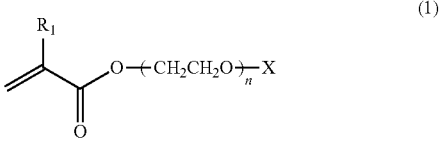

wherein $R_1$ is selected from the group consisting of H and alkyl groups having 1 to 3 carbon atoms, n is a number of 8 to 200, and X is selected from a group consisting of H and $CH_3$;

with at least one hydrophobic monomer selected from the group consisting of an acrylate monomer represented by chemical formula (2)

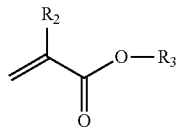

(2)

wherein $R_2$ is selected from the group consisting of H and alkyl groups having 1 to 3 carbon atoms, and $R_3$ is a substituent that has an alkyl group having 1 to 12 carbon atoms, and with an acrylamide monomer represented by chemical formula

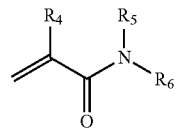

(3)

wherein $R_4$ is selected from the group consisting of H and alkyl groups having 1 to 3 carbon atoms, and $R_5$ and $R_6$ are independently selected from the group consisting of H and substituents that have an alkyl group having 1 to 18 carbon atoms;

and wherein (A) the molar ratio of the polyethylene oxide macromonomer to the total amount of acrylate monomer and acrylamide monomer ranges from 1:10 to 1:250;

(B) the radical co-polymerization is carried out in a mixture of water and one or more alcohols selected from the group consisting of ethanol, dipropylene glycol, 1,3-butylene glycol and isoprene glycol;

(C) the mass ratio of alcohols to water ranges from 9/1 to/9;

and (D) the total percentage by weight of the monomers represented by chemical formulas (1), (2) and (3) above is 100% of the total final copolymer.

2. The method for the preparation of an oil-in-water cosmetic according to claim 1, wherein the average particle size of the uncrosslinked core-corona microparticles is 50 to 400 nm.

3. The method for the preparation of an oil-in-water cosmetic according to claim 1, wherein the weight percentage of the monomers represented by chemical formulas (2) and (3) is from about 59% to about 84% relative to the total mass of the resulting co-polymer.

4. The method for the preparation of an oil-in-water cosmetic according to claim 2, wherein the weight percentage of the monomers represented by chemical formulas (2) and (3) is from about 59% to about 84% relative to the total mass of the resulting co-polymer.

5. An oil-in-water emulsified cosmetic prepared by the method for the preparation of an oil-in-water cosmetic of claim 1.

6. An oil-in-water emulsified cosmetic prepared by the method for the preparation of an oil-in-water cosmetic of claim 2.

7. An oil-in-water emulsified cosmetic prepared by the method for the preparation of an oil-in-water cosmetic of claim 3.

8. An oil-in-water emulsified cosmetic prepared by the method for the preparation of an oil-in-water cosmetic of claim 4.

9. The method for the preparation of an oil-in-water cosmetic according to claim 3, wherein the weight percentage of the monomer represented by chemical formula (1) is from 16% to 41% relative to the total mass of the resulting co-polymer.

10. The method for the preparation of an oil-in-water cosmetic according to claim 4, wherein the weight percentage of the monomer represented by chemical formula (1) is from 16% to 41% relative to the total mass of the resulting co-polymer.

* * * * *